(12) United States Patent
Kanesaka (10) Patent No.: US 6,524,321 B2
(45) Date of Patent: Feb. 25, 2003

(54) CLOSURE DEVICE FOR PUNCTURE IN VESSEL

(76) Inventor: Nozomu Kanesaka, 81 Greenwoods Rd., Old Tappan, NJ (US) 07675

( * ) Notice: Subject to any disclaimer, the term of this patent is extended or adjusted under 35 U.S.C. 154(b) by 155 days.

(21) Appl. No.: 09/752,735

(22) Filed: Jan. 3, 2001

(65) Prior Publication Data

US 2002/0087171 A1 Jul. 4, 2002

(51) Int. Cl.[7] .............................................. A61B 17/04
(52) U.S. Cl. ........................ 606/144; 606/145; 606/148; 112/169; 112/80.03
(58) Field of Search ................................ 606/144, 145, 606/147, 148; 112/169, 80.03

(56) References Cited

U.S. PATENT DOCUMENTS 5,836,955 A * 11/1998 Buelna et al. .............. 606/144
5,964,773 A * 10/1999 Greenstein ................. 606/144
6,206,893 B1 * 3/2001 Klein et al. ................ 606/139

* cited by examiner

Primary Examiner—John J. Calvert
Assistant Examiner—James G Smith
(74) Attorney, Agent, or Firm—Kanesaka & Takeuchi (57) ABSTRACT

A closure device for a puncture in a blood vessel is formed of a needle holder having a pair of first needle passages at a front side, and a needle catcher located at the front side of the needle holder to be movable thereto and having a pair of second needle passages aligned with the first needle passages. A pair of needle pushers is slidably located in the first needle passages, and a needle handle is attached to the needle pushers. A pair of needles joined with a suture is disposed in the first needle passages at a side close to the needle catcher. When the needle handle is actuated, the needles in the first needle passages are pushed by the needle pushers and transferred to the second needle passages. Thus, when wall portions are held between the needle holder and the needle catcher, the wall portions are sutured by the needles with the suture.

10 Claims, 8 Drawing Sheets

CLOSURE DEVICE FOR PUNCTURE IN VESSEL

BACKGROUND OF THE INVENTION AND RELATED ART STATEMENT

The present invention relates to a closure device used for a medical purpose, and more particularly, it relates to a closure device for suturing a puncture site in a blood vessel after an angioplasty procedure.

In angioplasty called percutaneous transluminal coronary angioplasty (PTCA), for example, a catheter having a balloon at the distal end (balloon catheter) is introduced into a body of a patient to enlarge a constriction in a vessel, such as a coronary artery. In order to introduce the catheter into the vessel, a small puncture is incised in a femoral artery, and a guide wire and the balloon catheter are introduced therefrom and guided to an aorta. Then, the guide wire and the balloon catheter are further pushed to a constriction in the coronary artery to enlarge the constriction.

After the PTCA procedure is completed, the guide wire and the catheter are withdrawn from the femoral artery, and the puncture in the femoral artery is treated to stop bleeding for several hours, such as four to seven hours. During this period, the patient has to lie on the bed in a hospital, resulting in wasting time for the patient and adding an additional cost for the procedure.

One of the most basic methods for closing the puncture is to apply pressure to the puncture site for 3 to 4 hours until bleeding stops, called "compression". In this method, the patient is immobilized on the bed for 6 to 10 hours.

The puncture may be manually sutured by a needle and a thread or suture, which can securely close the puncture. However, it is very difficult to master the technique for suturing the small puncture in the blood vessel manually, resulting in requiring a long learning. Also, it take time for the manual suturing.

Accordingly, in recent years, collagen plug devices and suturing devices have been developed to reduce the time for the patient to lie on the bed after the PTCA procedure. The collagen plug device is used for closing the puncture by the collagen plug. Although the collagen plug device is easy to use, it does not work well with a larger puncture, and a success ratio for closing the puncture is not desirable.

Figure 13:
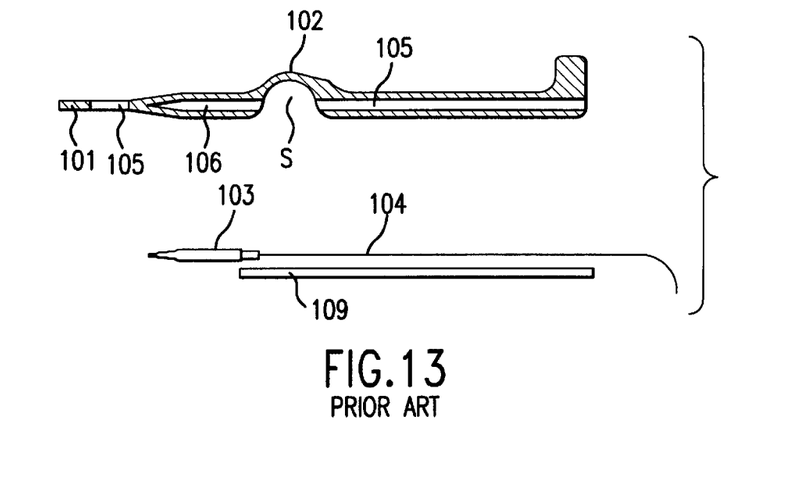
FIG. 13 is a schematic section view of a conventional suturing device.

The suturing devices have been developed in order to make the suturing easier. For example, as shown in FIG. 13, a conventional suturing device is formed of a shaft 101 with a bend area 102, and a needle 103 with a suture 104. The shaft 101 has a needle passage 105 for receiving the needle 103, a needle well 106, a guide wire passageway 107, and a space S between the needle well 106 and the needle passageway 105.

Figure 14:
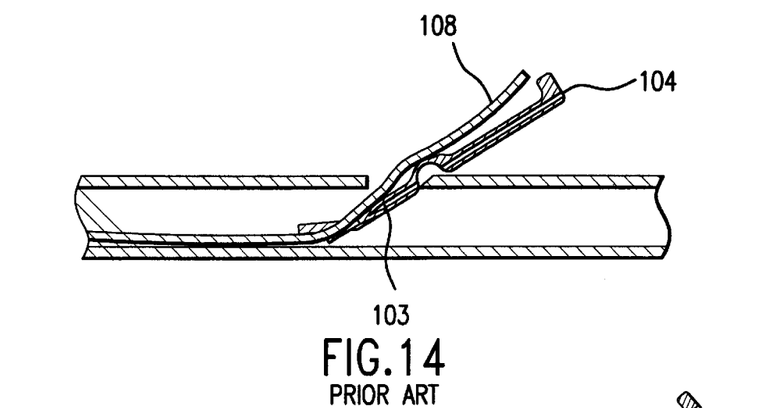
FIGS. 14 and 15 are schematic sectional views for showing the procedure of using the conventional suturing device.
Figure 15:
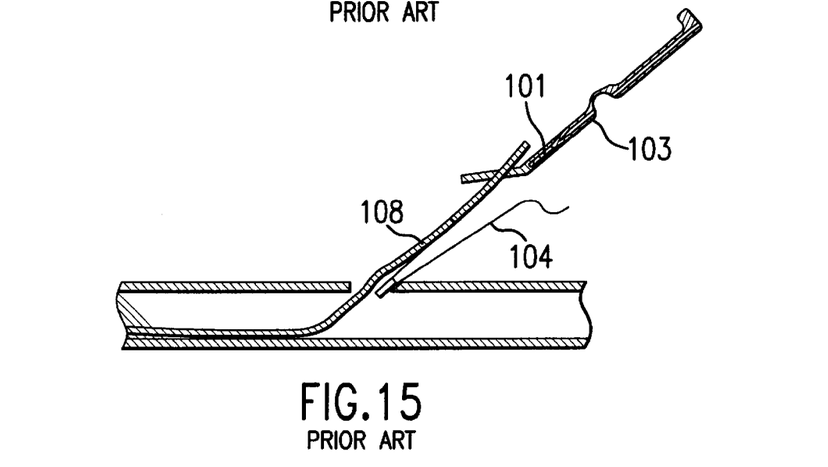

In the suturing device, after the PTCA procedure, the guide wire 108 used for guiding the balloon catheter is left in the vessel, and the shaft 101 is introduced into the vessel through the puncture by sliding the shaft 101 over the guide wire 108. The space S of the catcher 102 is located at the puncture to encompass a wall of the blood vessel, and the needle 103 with the suture 104 located in the needle passage 105 is pushed by a needle pusher 109 to enter the needle well 106 through the wall of the blood vessel in the space S. When the needle 103 is placed in the needle well 106, the needle pusher 109 is withdrawn from the needle passage 105 (in FIG. 14), and the suture is pulled away through the slit S. Then, the shaft 101 with the needle is withdrawn from the vessel through the puncture over the guide wire as shown in FIG. 15, so that the suture 104 attached to the needle 103 passes through the wall of the vessel to form one stitch.

Then, the needle 103 is removed from the needle well 106 and is placed in the needle passage 105 manually, and the above procedures is repeated at an opposite side of the puncture, so that the two portions with the puncture therebetween are sutured. Thereafter, the guide wire 108 is removed from the vessel, and a knot is made between the two ends of the suture to close the puncture.

In this conventional suturing device, however, there are the following problems. Firstly, in order to close the puncture by suturing, the suture must pass through the two portions beside the puncture, but the conventional suturing device can suture only one point at a time. Thus, after the needle with the suture passes through the one point, the needle with the suture has to be removed from the needle well by hand, and the needle with the suture has to be reintroduced into the needle passageway in the shaft. Then, the shaft has to be reintroduced into the vessel for suturing at the second portion, and the procedure for suturing has to be repeated. Thus, the operation of the conventional suturing device is cumbersome.

Secondly, it is effective for the suturing procedure to hold the vessel wall at the puncture while the suturing is made. In the conventional suturing device, however, although the space in the catcher helps positioning the shaft at the puncture site, the catcher can not sufficiently hold the vessel wall while suturing the vessel wall around the puncture.

In view of the problems in the conventional procedures, the present invention has been made, and an object of the invention is to provide a closure device for a puncture in a vessel, which can suture two portions beside the puncture at a time and is operated easily.

Another object of the invention is to provide a closure device as stated above, which can hold the vessel wall at the puncture securely while the needles pass through the vessel wall.

A further object of the invention is to provide a closure device as stated above, wherein the suturing can be done at once without handling the needle manually.

Further objects and advantages of the invention will be apparent from the following description of the invention.

SUMMARY OF THE INVENTION

A closure device for a puncture in a vessel, i.e. blood vessel, of the invention is basically formed of a needle holder having a pair of first needle passages at a front side, and a needle catcher located at the front side of the needle holder to be movable thereto. The needle catcher has a pair of second needle passages aligned with the first needle passages. Also, the closure device includes a pair of needle pushers or pushing shafts slidably located in the first needle passages, and a needle handle attached to the needle pushers for actuating the needle pushers.

In the invention, a pair of needles joined with a suture is disposed in the first needle passages at a side close to the needle catcher. When the needle handle is actuated, the needles in the first needle passages are pushed by the needle pushers and transferred to the second needle passages.

In operation, the closure device is located in the blood vessel such that the first needle passages are located above two wall portions of the vessel with a puncture hole therebetween. The needle handle is operated to push the needles to the second passages while passing through the wall portions of the vessel. Then, the closure device is removed from the blood vessel, and the suture passing through the two wall portions of the vessel are joined or tightened together. In this simple one procedure, the two wall portions are joined together by the suture. Thus, the closure device of the invention can be operated easily without skill.

The closure device of the invention further includes a guide shaft slidably disposed inside the needle holder and connected to the needle catcher. When the guide shaft is actuated, the needle catcher is moved relative to the needle holder. Thus, the wall portions of the blood vessel at the puncture can be securely held between the needle holder and the needle catcher when the needles pass therethrough.

The closure device further includes a needle catcher handle fixed to the guide shaft, and a spring disposed between the needle catcher handle and the needle holder for urging the needle catcher to be located close to the needle holder. Accordingly, the needle catcher can be handled easily.

In order to hold the needles with the suture, the needle holder includes slits at the front side to communicate with the first needle passages. Thus, the suture attached to the needles are located outside the needle holder.

The closure device of the invention further includes a nose tube at a front end of the needle catcher. The nose tube has a guide wire passage for accommodating a guide wire therein. Thus, the needle catcher can be located inside the blood vessel through the guide wire used for the PTCA procedure.

DETAILED DESCRIPTION OF PREFERRED EMBODIMENTS

Hereunder, embodiments of the invention will be explained with reference to the attached drawings.

Figure 1:
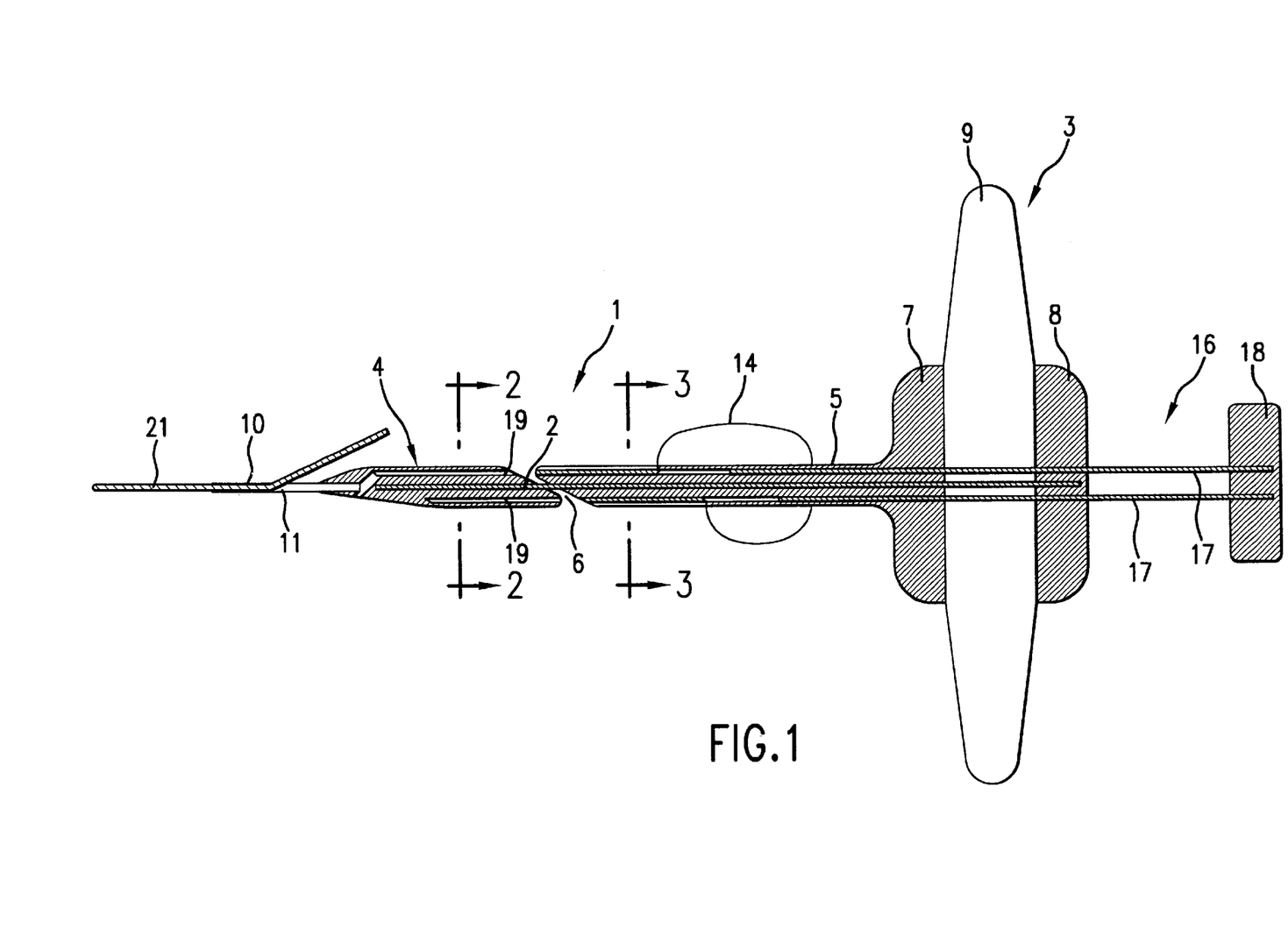
FIG. 1 is a sectional view of a closure device for a puncture in a vessel of an embodiment of the invention.

As shown in FIG. 1, a closure device for a puncture in a vessel or blood vessel of the invention is basically formed of a flat, elongated main body 1, a guide shaft 2 disposed inside the main body 1, and a handle portion 3 attached to a proximal end of the main body 1. The main body 1 is formed of a needle catcher 4, and a needle holder 5. The guide shaft 2 has a flat shape and is fixed to the needle catcher 4. The guide shaft 2 slidably passes throughout the entire area of the needle holder 5. Ends of the needle catcher 4 and the needle holder 5 facing each other are diagonally cut and are disposed to have a narrow space 6 therebetween. Since the guide shaft 2 has a flat shape and passes through the needle holder 5, the needle catcher 4 and the needle holder 5 keep the relative position as shown in FIG. 1. Namely, the needle catcher 4 does not rotate relative to the needle holder 5.

The handle portion 3 is formed of a needle holder handle 7 integrally formed with the needle holder 5, a needle catcher handle 8, and a spring 9 disposed between the needle holder handle 7 and the needle catcher handle 8. The rear end of the guide shaft 2 is fixed to the needle catcher handle 8. Also, a distal end of the body 1 is provided with a nose tubing 10 having a guide wire passage 11 therein.

Figure 5:
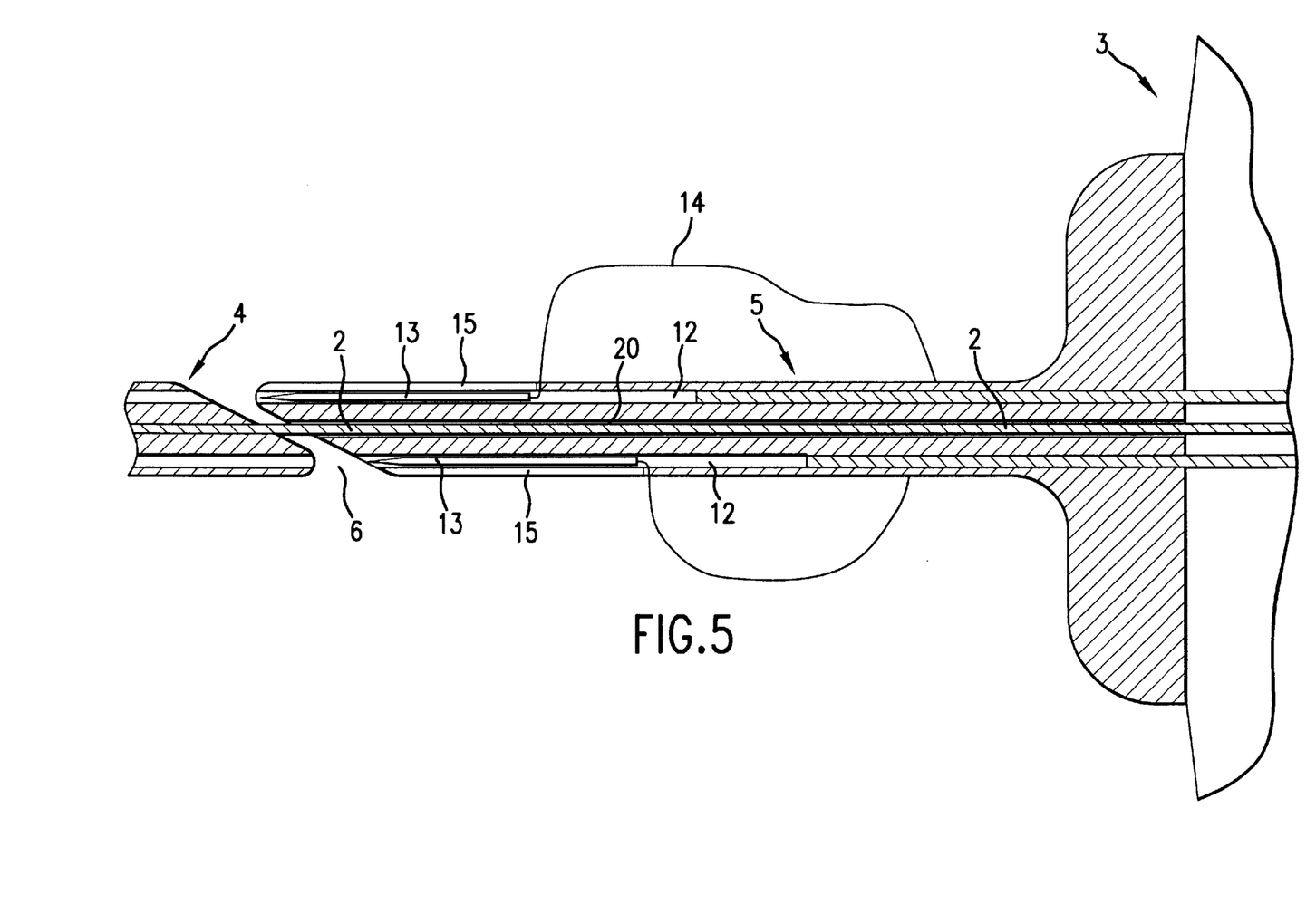
FIG. 5 is an enlarged sectional view for showing a middle portion of the closure device.

As shown in FIG. 5, a pair of needle passages 12 is formed in the needle holder 5, and a pair of needles 13 is placed in the needle passages 12. Also, the needle holer 5 includes slits 15 at the front or distal end thereof to partly communicate with the needle passages 12. Ends of a single suture 14 is attached to proximal ends of the needles 13, and the suture 14 is placed outside of the shaft 1 through the slits 15. The needles 13 with the suture 14 are disposed in the needle passages 12 in advance, as shown in FIG. 1.

Also, the closure device of the invention is provided with a needle pusher 16 formed of a pair of elongated pusher shafts 17 and a pusher handle 18 attached to proximal ends of the pusher shafts 17. The pusher shafts 17 are slidably placed in the needle passages 12 behind the needles 13, as shown in FIG. 1. The pusher shafts 17 extend rearwardly through the needle holder handle 7 and the needle catcher handle 8, and are fixed to the pusher handle 18. When the pusher handle 18 is moved, the pusher shafts 17 advance or retract in the needle holder 5.

Figure 2:
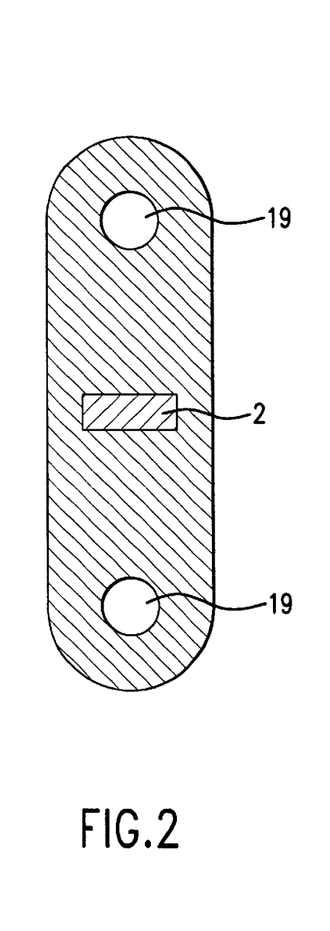
FIG. 2 is an enlarged sectional view taken along line 2—2 in FIG. 1.
Figure 3:
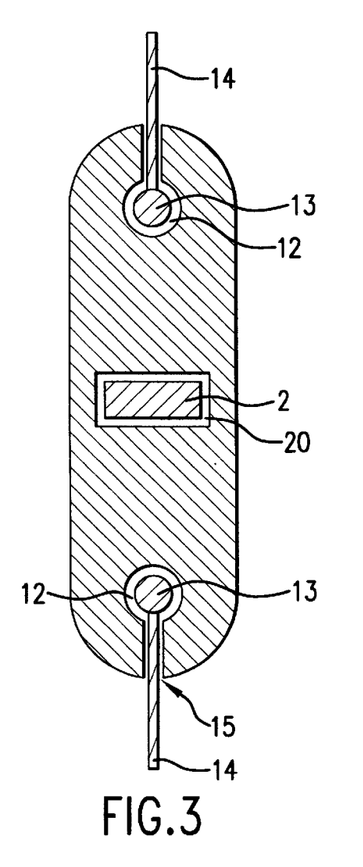
FIG. 3 is an enlarged sectional view taken along line 3—3 in FIG. 1.
Figure 4:
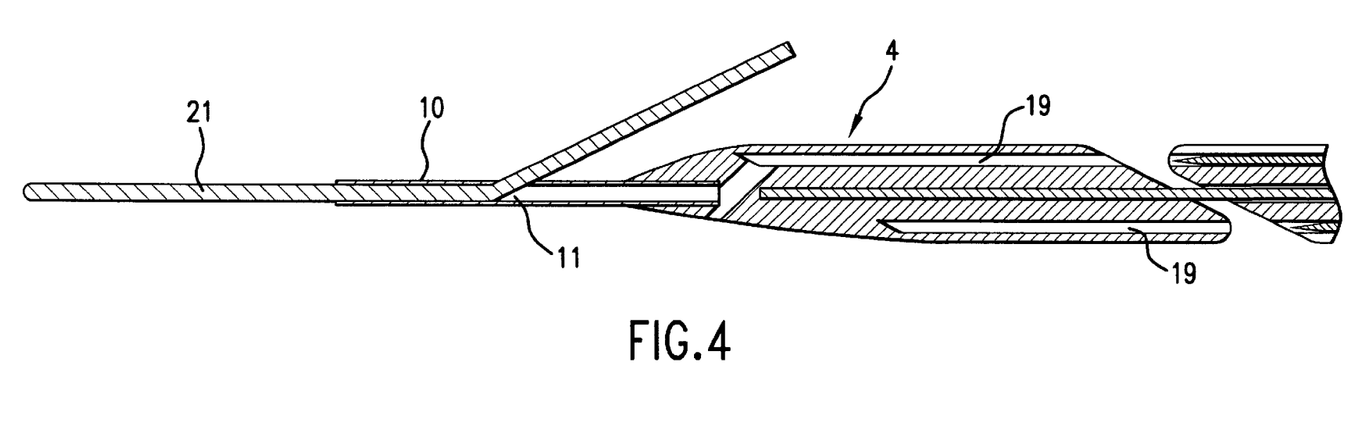
FIG. 4 is an enlarged sectional view of a distal end portion of the closure device.

As shown in FIG. 2 and FIG. 4, the needle catcher 4 includes a pair of needle wells 19 aligning with the needle passages 12 for receiving the needles 13 when the needles 13 are pushed to be located in the needle catcher 4. The end of the guide shaft 2 is located in and fixed to the needle catcher 4, as shown in FIG. 2.

Figure 6:
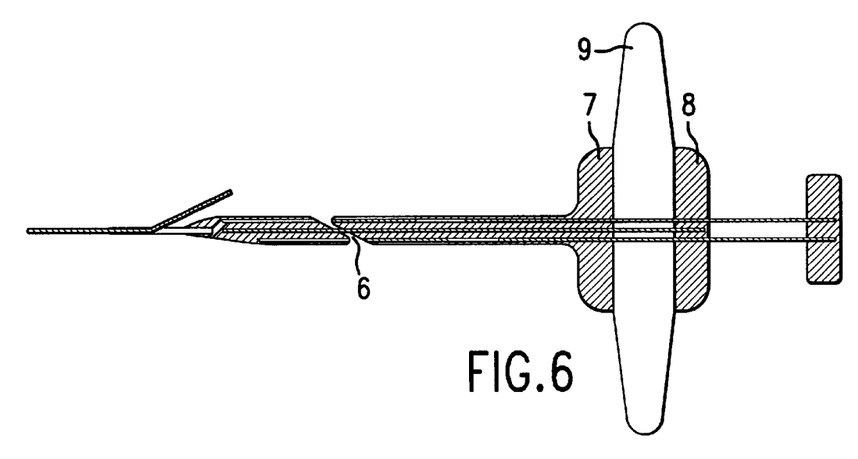
FIG. 6 is a sectional view of the closure device in a normal condition.
Figure 7:
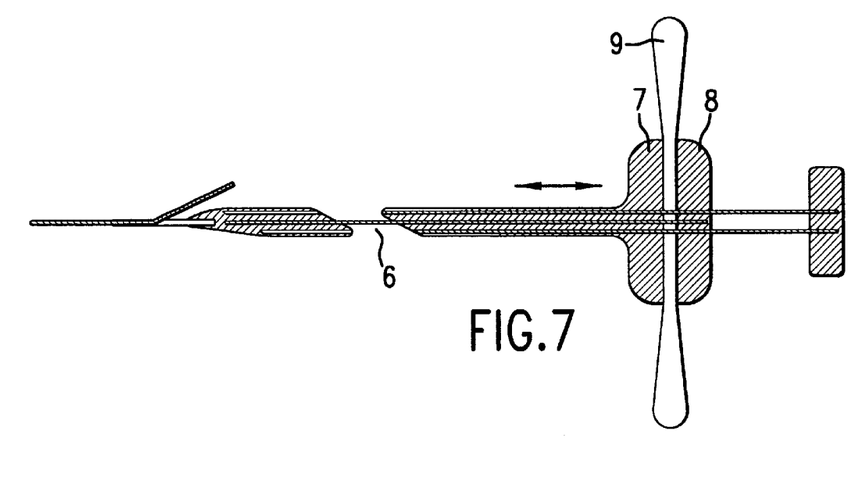
FIG. 7 is a sectional view of the closure device in a condition that a needle holder handle is squeezed to a main handle.

In the closure device shown in FIG. 6, the needle holder handle 7 and the needle catcher handle 8 are located slightly spaced apart from each other with a relatively narrow space 6. When the needle catch handle 8 is squeezed or pushed relative to the needle holder handle 7, the spring 9 is contracted, and the space 6 between the needle catcher 4 and the needle holder 5 is enlarged as shown in FIG. 7. When the squeezing force with respect to the needle holder handle 7 is released, the needle catcher handle 8 is returned to the position shown in FIG. 6 by a returning force of the spring 9.

Normally, the closure device is manufactured to have all the parts including the needles with the suture assembled together as shown in FIG. 1, which is ready to use. The closure device is disposed after use.

After the PTCA or other procedure, a guide wire 21, which is generally used in the PTCA procedure, is left at a puncture in the vessel, and the closure device of the invention as shown in FIG. 1 is used. Namely, the guide wire 21 is placed in the nose tubing 10 and the needle catcher 4 is introduced into the blood vessel 31 through the puncture in the vessel. While the needle catcher 4 is introduced into the vessel, the faces of the needle catcher 4 and the needle holder 5 are oriented to be parallel to the vessel wall 30 (shown in FIG. 8). Once the needle catcher 4 is placed in the vessel 31, the guide wire 21 is removed from the vessel slowly.

Then, the needle catcher handle 8 is pushed to enlarge the space 6 between the needle catcher 4 and the needle holder 5, and is released to securely hold two wall portions of the vessel 31 in the space 6 between the needle catch 4 and the needle holder 5. Thus, the vessel wall 30 can be securely caught between the needle catcher 4 and the needle holder 5.

Figure 8:
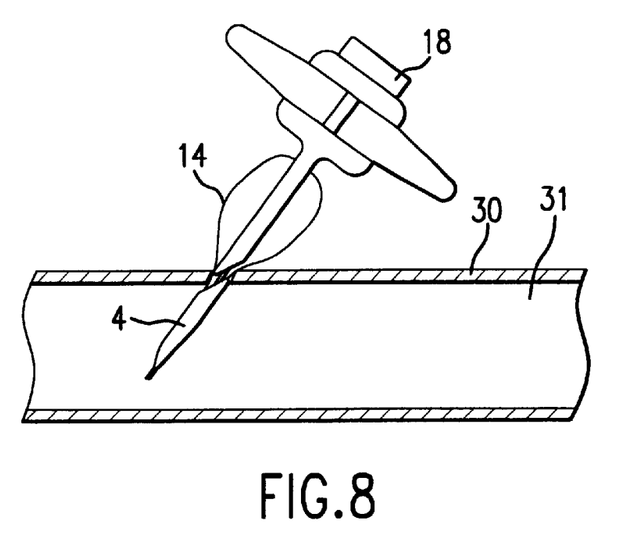
FIG. 8 is an explanatory view schematically showing the closure device of the embodiment placed in a vessel.

Then, the needle pusher handle 18 of the needle pusher 16 is pushed against the needle holder 5, so that the pusher shafts 17 push the needles 13 with the suture 14 placed in the needle passages 12 in the needle holder 5. Therefore, the needles 13 with the suture 14 pass through the vessel wall 30 at two portions beside the puncture, that is, two locations having the puncture therebetween, and the needles 13 are transferred to the needle wells 19 in the needle catcher 4. This condition is shown in FIG. 8.

Figure 9:
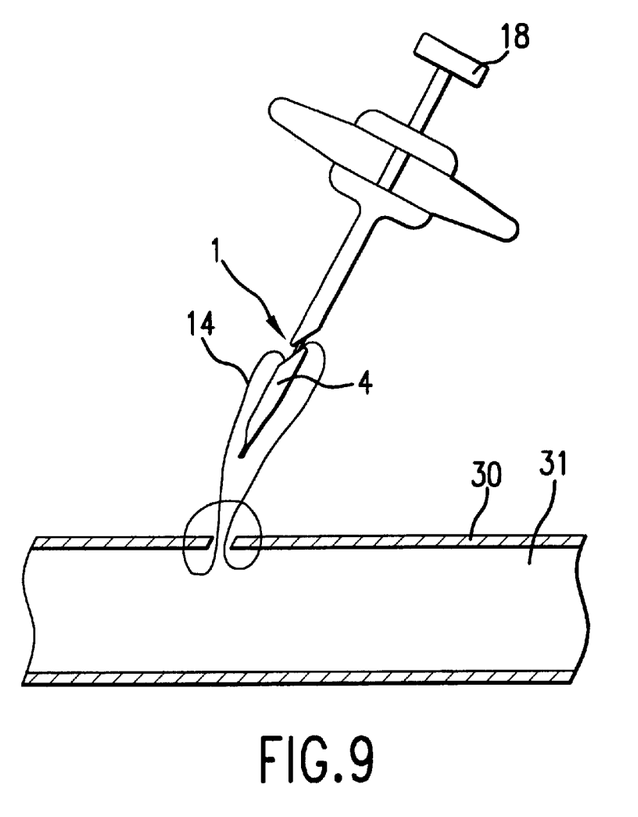
FIG. 9 is an explanatory view schematically showing that the closure device is withdrawn from the vessel after two portions of the vessel are sutured.

Thereafter, the pusher handle 18 is withdrawn rearwardly so that the pusher shafts 17 are located back to the needle passages 12 in the needle holder 5. Then, the entire closure device is rotated for 90 degrees to align the needles along the cut line of the puncture. Thereafter, the needle catcher 4 is slowly withdrawn from the vessel through the puncture. In this condition, two suture lines project from the puncture as shown in FIG. 9.

In order to close the puncture, the suture lines may be cut and simply tightened together. If the puncture is tightened together with several suture lines, after the closure device is removed from the vessel, another closure device is introduced into the vessel through the puncture. Then, the same procedure is repeated to suture the puncture and take out the suture lines. Finally, all the suture lines are tightened together.

Figure 10A:
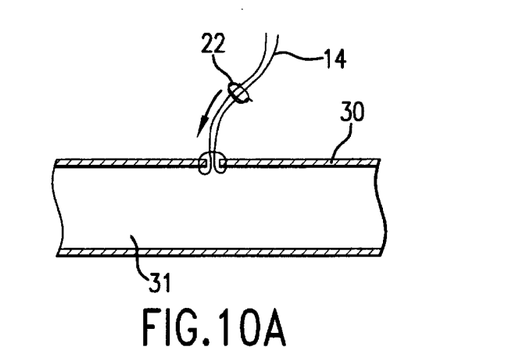
FIGS. 10A and 10B are explanatory views showing that collagen strings placed over the suture are used for closing the puncture.
Figure 10B:
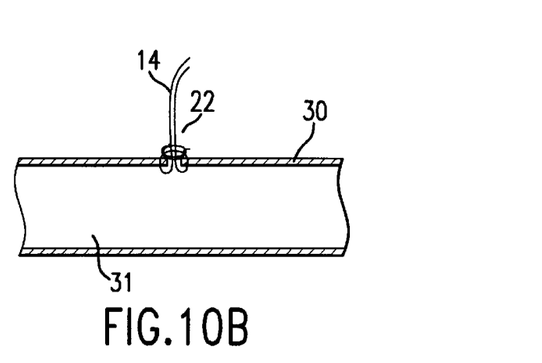
Figure 11A:
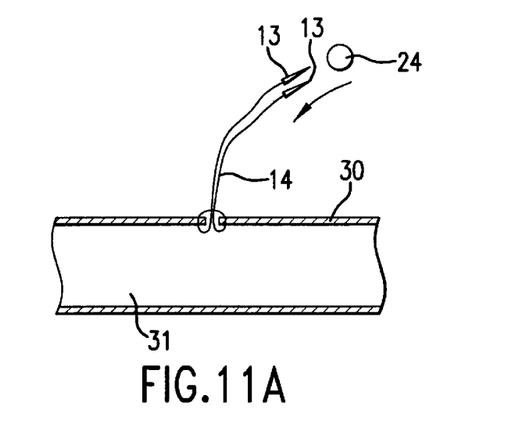
FIGS. 11A and 11B are explanatory views showing that a collagen plug is used for closing the puncture.
Figure 11B:
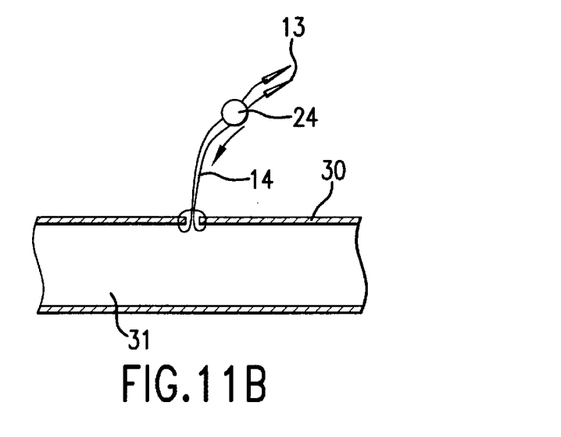

When the puncture is closed with the suture 14, a knot 22 made of a collagen string may be made on the suture 14 as shown in FIG. 10A, and the knot 22 is pushed against the vessel wall 30, as shown in FIG. 10B. Alternatively, a collagen plug 24 known in the art can be used instead of the knot 22. In this case, as shown in FIGS. 11A and 11B, the suture lines pass through the collagen plug 24 by using the needles 13, and the collagen plug 24 is pushed onto the puncture so as to reinforce the closing of the puncture by the suture 14. Finally, the suture lines are tightened to place the collagen plug 24 over the puncture.

Figure 12A:
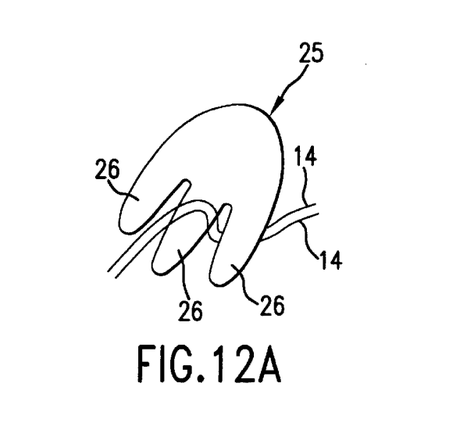
FIGS. 12A and 12B are explanatory views of a tensioner which helps closing the puncture tightly.
Figure 12B:
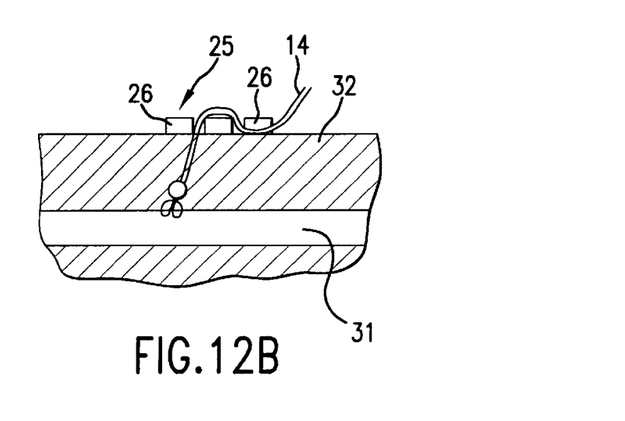

Also, after the closing of the puncture by one of the aforementioned methods, a tensioner 25 shown in FIG. 12A may be placed outside the patient's body to apply the tension to the suture 14 until the bleeding stops. The tensioner 25 has a plurality of projections 26, and the suture 14 outside the body is engaged with the projections 26 as shown in FIG. 12A. The tensioner 25 pushes a skin 32 of the patient's body above the puncture in the vessel 31. When the bleeding stops, the suture 14 outside the patient's body is cut, and the tensioner 25 is removed.

According to the closure device for a puncture in a vessel of the invention, since the closure device includes a pair of needles with a suture therein, two locations beside the puncture in the vessel can be sutured at once, so that the suturing of the puncture in the vessel can be done very easily.

Also, since the closure device of the invention is provided with the handle portion, the space in the device for holding the vessel wall can be changed, and the vessel wall can be held securely while suturing the vessel wall beside the puncture.

While the invention has been explained with reference to the specific embodiments of the invention, the explanation is illustrative and the invention is limited only by the appended claims.

What is claimed is:

1. A closure device for a puncture in a vessel, comprising:

a needle holder having a pair of first needle passages at a front side, a needle catcher located at the front side of the needle holder to be movable thereto, said needle catcher having a pair of second needle passages aligned with the first needle passages, a pair of needle pushers slidably located in the first needle passages, and a needle handle attached to the needle pushers to actuate the same for allowing needles in the first needle passages to be transferred to the second needle passages.

2. A closure device according to claim 1, further comprising a guide shaft slidably disposed inside the needle holder and fixed to the needle catcher so that when the guide shaft is actuated, the needle catcher is moved relative to the needle holder.

3. A closure device according to claim 2, further comprising a needle catcher handle fixed to the guide shaft, and a spring disposed between the needle catcher handle and the needle holder for urging the needle catcher to be located close to or away from the needle holder.

4. A closure device according to claim 3, wherein said needle holder includes slits disposed at the front side and communicating with the first needle passages for allowing a suture attached to the needles to be located outside the needle holder.

5. A closure device according to claim 4, further comprising a pair of needles joined with the suture, said needles being disposed in the first needle passages at a side close to the needle catcher so that when the needle handle is actuated, the needles in the first needle passages are pushed by the needle pushers and transferred to the second needle passages.

6. A closure device according to claim 5, wherein the suture is respectively connected to rear ends of the needles.

7. A closure device according to claim 4, further comprising a nose tube at a front end of the needle catcher, said nose tube having a guide wire passageway for receiving a guide wire therein.

8. A closure device according to claim 7, wherein said needle handle is located at a rear side of the needle catcher handle, said needle pushers passing through the needle holder and the needle catcher handle and engaging the needle handle.

9. A closure device according to claim 8, wherein said needle catcher and the needle holder have end portions facing each other, said end portion being cut diagonally.

10. A closure device according to claim 9, wherein said needle catcher and the needle holder have elongated shapes in section perpendicular to a longitudinal direction thereof.

* * * * *